United States Patent [19]

Herbold

[11] 4,142,520

[45] Mar. 6, 1979

[54] TILTABLE RECLINING AND SEATING DEVICE

[76] Inventor: Ted E. Herbold, 1909 E. 28th Ave., North Kansas City, Mo. 64116

[21] Appl. No.: 818,610

[22] Filed: Jul. 25, 1977

[51] Int. Cl.[2] .................... A61F 5/00

[52] U.S. Cl. .................... 128/74; 269/325

[58] Field of Search .................... 128/69-74; 269/322-328; 5/66, 67

[56] References Cited

U.S. PATENT DOCUMENTS

| | | | |
|---|---|---|---|
| 1,530,719 | 3/1925 | Harris | 128/74 |
| 2,598,204 | 5/1952 | Allen | 128/74 X |
| 3,210,779 | 10/1965 | Herbold | 5/66 |
| 3,568,669 | 3/1971 | Stites | 128/71 |

*Primary Examiner*—John D. Yasko

*Attorney, Agent, or Firm*—Thomas M. Scofield

[57] ABSTRACT

Improvements in devices for reclining the incumbent human body in an inclined, head-downward position; improvements in foot-ankle suspension systems for use in such body reclining and inclining devices; improvements in hand operated mechanisms permitting the user of the device to control the rate and degree of recline in such devices; locking means for releaseably securing the device in horizontal and fully inclined positions.

8 Claims, 12 Drawing Figures

TILTABLE RECLINING AND SEATING DEVICE

BACKGROUND OF THE INVENTION

It is believed to be well established that periodically subjecting the individual human body to a recumbent, head-downwards position for limited periods of time has beneficial and important health effects. Numerous devices have been developed over the years for achieving this position. A number of these devices are recorded in the Patent art, as seen in the second category or Class of prior art listed herebelow. The following remarks are intended to give a rationale to the operation of the instant device, in addition to those beneficial effects, premises and goals set forth in the prior art, which rationales and benefits will not here be repeated, but which are incorporated by reference. Applicant is specifically referring to the physiological and health effects and benefits which result from a reclined, head-downward position, with the weight of the body preferably being suspended from the feet or ankles of the individual.

A reversed gravity theory may be postulated to the effect that men are victims of a natural, inherent handicap causing accelerated physical deterioration that should not be wholly attributed to old age. Specifically, man's vertical posture, as effected by the pull of gravity and increased in many cases by obesity, eventually creates a pinching and choking effect both on the nerves and blood vessels, particularly at points where they emerge through the openings between the vertebrae in the spinal column. Such a theory is supported not only by anatomical and physiological evidence, but also by plausible supposition.

Thus, the length of the spinal column, in the average adult male, at about the age of 30, is substantially 28 inches. It is curved and flexible and held together by muscles and ligaments. Separating each of the 26 adjacent vertebrae is an intervertebral disk, made up of tough, fibrous cartilage. The total thickness of all of these disks, placed one on top of the other, is approximately 5 inches.

Through a vertical hole (spinal foramen) in each vertebra runs the spinal cord which extends from the lower brain down to the coccyx. This cord consists of 31 pairs of nerve segments bound together like a cable. The 31 pairs of nerve segments, excepting the first cervical nerve pair, emerge outwardly through the openings between each vertebrae and continue through muscles and ligaments to the various parts of the body, thus giving 30 nerve segments on each side of the spine. The named openings are supported by the intervertebral disks discussed above. Also through each of these same openings passes a vein and an artery to supply the spinal cord with its necessary blood supply. The emerging nerves of voluntary and involuntary reaction branch out to supply the skin, bodily organs and glands their life functioning impetus.

Statistics of the U.S. Department of Health, Education and Welfare show that the average man shrinks in height over three inches between the ages of 30 and 79. This shrinkage mostly occurs with respect to the intervertebral disks, since the bones themselves do not shrink. Thus, apparently, three inches of shrinkage occurs in what was originally about 5 inches of cartilage, over a 50 percent shrinkage. This theory postulates that, as this shrinkage occurs, a pinching effect emerges and develops on the nerves and blood vessels at the points where they emerge from the spinal cord. Such would naturally hamper their functional ability, resulting in slow physical deterioration to muscles, glands and organs they serve.

It is a postulate of the reverse gravity theory that, if the spinal column is periodically depressurized, by inverting the bodily position, with, as a result, relief of the described pinching under controlled stretch treatments, the particular nerves and blood vessels will have a chance to restore themselves and react as they should. At the same time, the blood supply will be increased to the upper extremities and the head.

The subject device is directed to achieving the described effects in the most efficient, safe and benefical manner. The degree of body incline can be regulated as desired between horizontal and a maximum inclination which is far from the vertical, yet sufficient to achieve the desired effects within a reasonable time. The stretching of the elements of the body with respect to one another is provided by the pull of the body weight alone, that is, no traction is employed. The effort involved requires no more than five to ten minutes a day, preferably just before retiring. Thus, if one goes to bed after use of the device, the spine does not quickly rebound to its former tight position, as the body, in a horizontal position, tends to nullify the gravity pull until the next morning, at least.

The goal is to provide a device whereby, through a series of such treatments, hopefully the youthful process is prolonged or restored, the aging process is relatively arrested and a general improvement in body appearance, muscle tone and general well being may be noticed and achieved.

THE PRIOR ART

Basically, the subject improvement is a development of the structure and device of my U.S. Pat. No. 3,210,779 "Multiple Position Combination Chair Bed," issued Oct. 12, 1965. Specifically, the instant device improves the means and apparatus for the head-down position of the device illustrated schematically in FIG. 7 of my Patent. There is other related prior art which, basically, divides into essentially three types of devices.

The first of these are Patents related to beds (typically hospital beds) adaptable to movement of a patient supporting frame into Trendelenburg and reversed Trendelenburg positions. Examples of these types of devices are seen in the following U.S. Pat. Nos.:

Turko et al 3,611,452, issued Oct. 12, 1971 "Invalid Bed Construction;"

Szucs 3,678,519, issued July 25, 1972 for "Hospital Bed;"

Kirkland 3,711,876, issued Jan. 23, 1973 for "Tilt Bed;" and

Saternus 3,722,010, issued Mar. 27, 1973 for "Adjustable Hospital Bed . . . ."

A second Class of devices, boards, couches, apparatus, tables or beds is directed to essentially the same goal as the subject device. Specifically, these devices are adapted to recline the recumbent human body into a tilted, head-downward position for therapeutic and healthful effects. The following U.S. Pat. Nos. exemplify this type of device:

Hoppe 2,176,342 issued Oct. 17, 1939 for "Health Balancing Board;"

Sprague 2,932,038 "Couch," issued Apr. 12, 1960;

De Girolamo 3,081,085 "Back Posture And Stretch Board," issued Mar. 12, 1963;

Heisler et al 3,152,802 "Therapeutic And Body Exercising Apparatus," issued Oct. 13, 1964;

Jennings 3,351,051 "Treatment Table With Rocking Means," issued Nov. 7, 1967;

Stites 3,568,669, issued Mar. 9, 1971 for "Tilting Health Table;"

Kotter 3,579,671 "Adjustable Bed," issued May 25, 1971; and

Bolmberg 3,588,929 "Adjustable Tilting Device . . . ," issued June 29, 1971.

Finally, there are devices, typically medical, for positioning patients in various reclining positions, including hospital beds, operating tables, hospital tables and the like. Exemplary of these are U.S. Pat. Nos.:

Hawk 1,529,699, issued Mar. 17, 1925 "Adjustable Hospital Bed;"

Alopaeus 2,186,660 "Operating Table," issued Jan. 9, 1940;

Climo 2,763,520, issued Sept. 18, 1956 "Rollable And Tiltable Hospital Table;"

Ohrberg 3,293,667, issued Dec. 27, 1966 "Adjustable . . . Tilting . . . Bed;" and 3,789,437, Garte, issued Feb. 5, 1974 for "Folding Hospital Bed."

OBJECTS OF THE INVENTION

A first object of the invention is to substantially improve the device of my U.S. Pat. No. 3,210,779 "Multiple Position Combination Chair Bed," issued Oct. 12, 1975, with respect to the features illustrated in FIGS. 6 and 7 thereof.

Another object of the invention is to substantially improve the devices of the prior art which are directed to means for reclining the recumbent human body in a downwardly angled, head-down position for healthful and therapeutic effects.

Another object of the invention is to provide an improved reclining frame for use in the device of the character described, whereby not only is the entire weight of the subject or operator suspended from the feet or ankle zone of the individual, but, additionally, a protective guard is provided at the head end of the device for limiting the downward inclination of the body supporting frame and obviating any chance of the head of the subject or operator contacting or striking the floor or ground zone.

Another object of the invention is to provide improved means for variably reclining a normally horizontal, body receiving frame, so that the said body-receiving frame may be reclined at any desired angle from horizontal to the maximum angle of recline without slippage and with complete safety, the body-receiving frame being returnable to a horizontal position or reclined to the greater angle after reaching a given angle of recline.

Another object of the invention is to provide such an improved frame with locking means which come fully into action when the device reaches its maximum angle of recline and automatically retracts upon return to the horizontal position, there being a built-in delay or take up in the lock for increased safety.

Another object of the invention is to provide such a drive system for a reclinable body-receiving frame which permits the recumbent operator or individual reclining on the frame to not only move the device from the horizontal to a partly or fully reclining position, but also return same readily to the horizontal position with a minimum of effort and discomfort.

Another object of the invention is to provide improvements in the art of reclining chairs, wherein the said reclining chair is tiltable to the maximum degree of the reclining body-receiving frame and returnable therefrom by simple, wheel operated means.

Another object of the invention is to provide such a device of the character described which is relatively simple in construction, fabricated of a minimum number of parts, rugged in use, service and operation, relatively cheap to manufacture and which has a long life of use and operation without requirement of replacement or repair of the parts. All of the parts of the device are readily available at all times and visible for inspection, adjustment and repair as required without any difficulty of access.

Other and further objects of the instant invention will appear in the course of the following description thereof.

THE DRAWINGS

In the drawings, which form a part of the instant specification and are to be read in conjunction therewith, an embodiment of the invention is shown and, the various views, like numerals are employed to indicate like parts.

DESCRIPTION OF STRUCTURE AND FUNCTION

The subject device includes a base support, an elongate flat frame pivotably mounted on the base support and means for tilting the frame with respect to the base support and then returning the frame to a normally horizontal position. The specific structure of this device will first be described and thereafter its operation and function.

Figure 1:
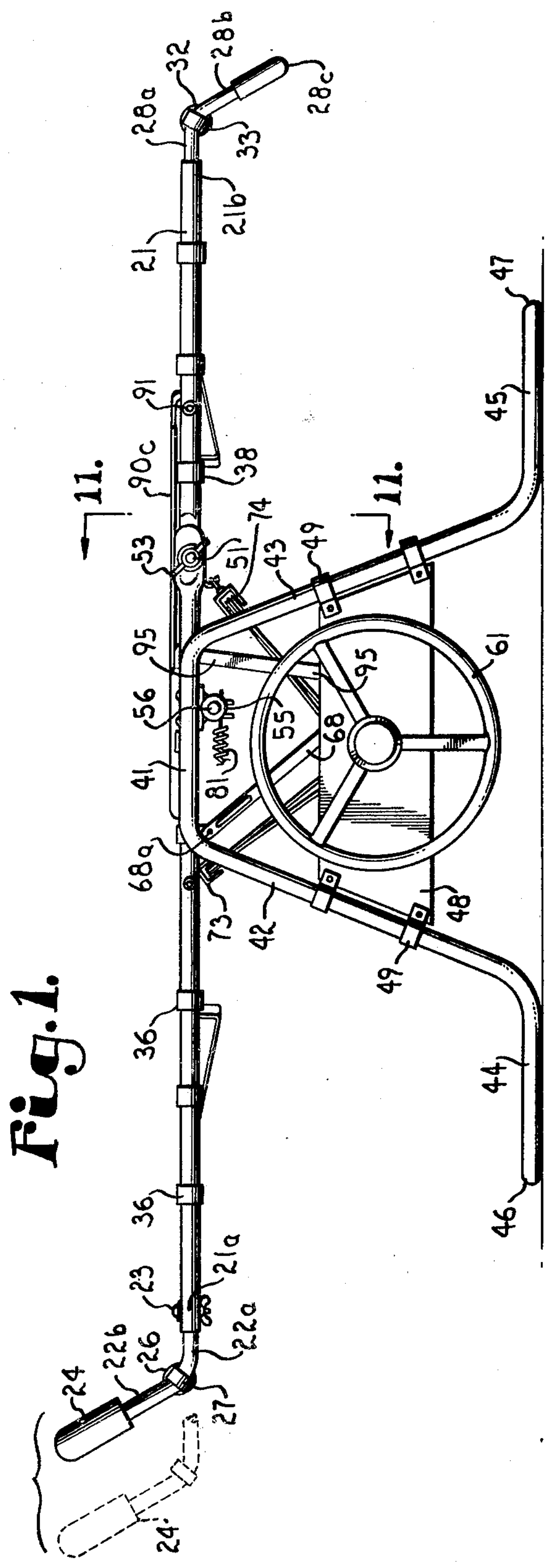
FIG. 1 is a side elevation of the subject device in horizontal or level position of the body-receiving frame, the dotted line showing in the left hand portion of the figure illustrating length extension.
Figure 2:
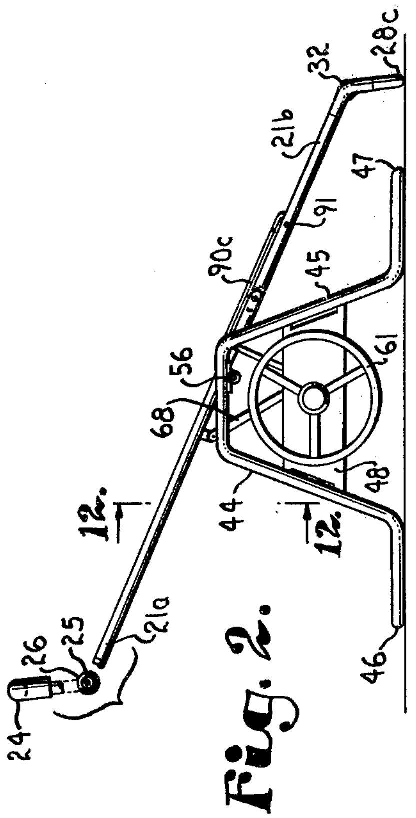
FIG. 2 is a view like that of FIG. 1, but with the body-receiving frame of the device angled so that the foot end is up and the head end is down.
Figure 3:
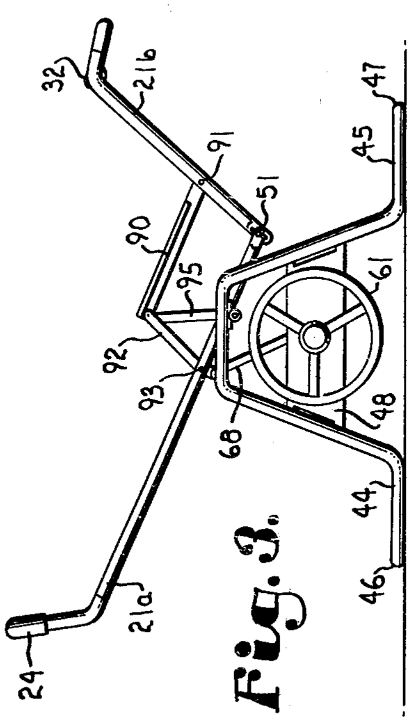
FIG. 3 is a view like that of FIG. 2, but with the chair back section elevated to produce a reclining sitting position, with the feet up.
Figure 4:
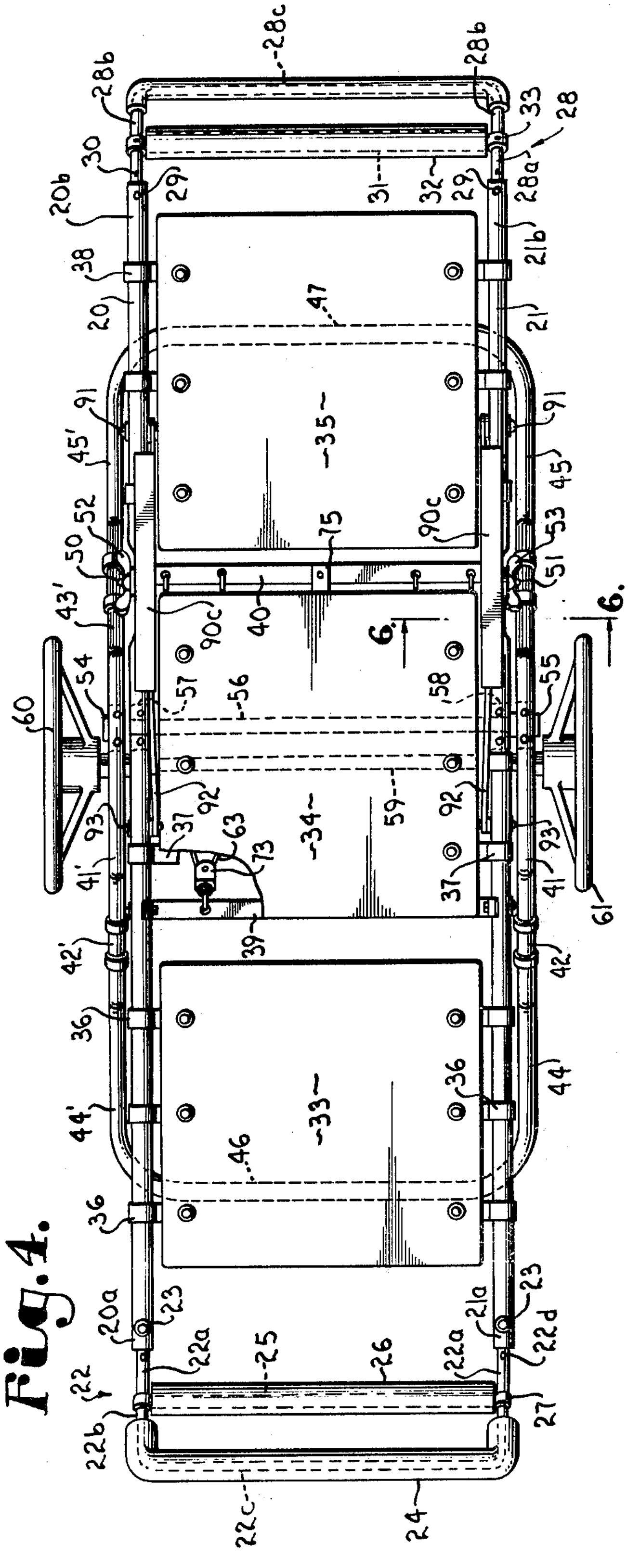
FIG. 4 is a plan elevation of the device in the position of FIG. 1 with a portion thereof cut away for illustrative purposes and the normally present cushioning pad (for comfort purposes) removed to show the frame construction.

The elongate, normally horizontal frame is seen in side view in three positions in FIGS. 1, 2 and 3 and in plan view from above in FIG. 4. Basically, this frame comprises a pair of elongate, parallel and normally horizontal hollow metallic sleeves of aluminum, stainless steel or the like 20 and 21. A first U-shaped (in the plan view of FIG. 4) member 22 is made up of a configured hollow sleeve which is adapted to insert into hollow sleeve ends 20*a* and 21*a* at its ends 22*a*. The ends 22*a* may be adjustably fixed along their length with respect to sleeves 20 and 21 by set screws or bolts 23 which removably engage spaced openings 22*d* (FIG. 4) along the length of ends 22*a*. The outboard leg ends of U-member 22 are upwardly angled at 22*b*. The base 22*c* of U-member 22 is most preferably covered by a resilient rubber or foam composition sleeve 24. An elongate rod 25, also preferably foam or rubber sleeve 26 covered, is strapped as at 27 to U-member 22 at the base of its upwardly angled portions 22*b*. Rod or beam 25 may be adjusted on the leg portions 22*b* and 22*a* by the provision of openings through the leg portions 22*a* and 22*b* and bolts through straps 27 (not seen). This permits adjustment for foot size of the user.

At the other (head) end of the frame, member 22 being at the foot end of the frame, this structure is essentially duplicated, with U-member 28 having inboard leg portions 28*a* received in sleeve ends 20*b* and 21*b*, angled outboard leg portions 28*b* and U-base leg 28*c*. Again, set screws or bolts 29 engage openings 30 along the legs 28*a* of U-member 28 for adjustable positioning of U-member 28. Transverse rod or bar 31 is preferably foam or rubber sleeve 32 covered and is strapped to the angle juncture of U-member portions 28*a* and 28*b* as at 33. Straps 27 and 33 may be themselves adjusted along the length of the legs of U-member 28 by virture of holes therethrough and bolts or screws through the straps (not shown).

As may particularly be seen in FIGS. 1–4, inclusive, the foot end or member 22 is upwardly angled at its outboard end and the head end (member 28) is downwardly angled. Member 28*c* may be cushioned to protect a floor, if desired.

Body carrying, transverse support members comprising three rigid plates 33, 34 and 35 (foot end, center and head end of the frame) are provided spaced along the length of the sleeves 20 and 21 and have sets of straps 36, 37 and 38 rigidly fixing same to sleeves 20 and 21. Yet further, a pair of transverse beam members 39 and 40 are provided which each extend between and are fixed to the sleeves 20 and 21 intermediate the ends thereof and spaced with respect to the pivoting and operating shafts in a manner which will be described. Accordingly, it is seen that the entire horizontal frame construction is quite rigidly and strongly constructed with sleeves 20 and 21 connected together (and braced apart) at a multiplicity of positions along their lengths.

The upward angling of foot member 22 and the provision of rod 25 (as well as the preferred cushioning of member 22*c* and member 25 at 24 and 26) is to enable the user of the device to insert his feet between members 22*c* and 25 with the toes of the user's feet hooked outboard of member 22*c* against foam padding 24 and the heels outboard past member 25 and against padding 26 with the ankles of the user's feet (and Achille's tendons of the user) overlying the foam padding 26 on member 25. Also preferably, the user's feet are pushed to the left and right, respectively, to insure that the upper portions of the user's feet also abut against the padding 22 at the corners to give more suspension support. Rod or shaft 31 is preferably padded so that one's head may be in contact with it. Preferably a padded cushion of integral character (not shown) is provided overlying the length (and slightly therepast) of all three plates or surfaces 33–35, inclusive, means being provided to tie the side edges of the padded cushion to sleeves 20 and 21 for removably attachment thereto. This is for comfort purposes, strictly.

The downward angling of the head end member 28 is to provide a contact with the base or floor on which the device is mounted below the head level of the user of the device.

The base of the device essentially comprises a pair of A-frame members which are parallel oriented and adapted to rest on a floor or ground surface with the lower ends of the legs of the A's. In the drawings, the flat, horizontal tops of the A-members are designated 41 and 41′, respectively, the side legs of the A-members being designated 42 and 43 (42′ and 43′) and the foot or lower end members of the A-supports numbered 44 and 45 (44′ and 45′). The lower floor contacting A-support member legs are connected at their outboard ends by transverse portions 46 and 47, thus giving a rigid, stable support for the normally horizontal frame previously described, when the connecting shafts to be described are also considered. Mounted between and rigidly strapped or connected to the downwardly extending A-support frame members 42 and 43 (42′ and 43′) are rigid metallic plates 48 having securing strap members 49 making rigid connection of plates 48 with the leg members 42 and 43 (42′ and 43′). The purpose of plates 48 is to brace the legs 42 and 43 (42′ and 43′) and, additionally, carry an operating shaft therebetween to be described.

Figure 5:
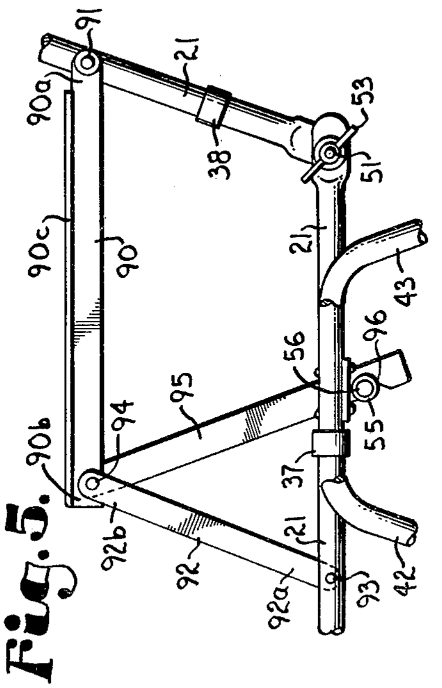
FIG. 5 is an enlarged, fragmentary side view of the device with the chair back raised, but with the device in level position. This is a view of the substantial upper center of the device as seen in FIG. 1 with, as noted, the chair back raised as in FIG. 3.
Figure 6:
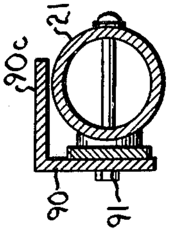
FIG. 6 is a view taken along the line 6—6 of FIG. 4 in the direction of the arrows.
Figure 10:
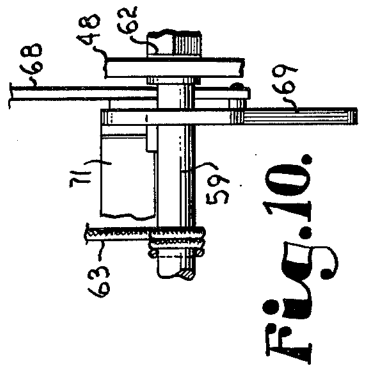
FIG. 10 is a view taken along the line 10—10 of FIG. 8 in the direction of the arrows.

Sleeve members 20 and 21 are divided into two parts at the connection of transverse beam member 40 in order to permit the upward pivoting of the head end of the frame to the chair back position of FIGS. 3 and 5. Accordingly, in the zone of their length mentioned (at transverse beam 40), the walls of sleeves 20 and 21 are flattened and pivotably engaged by bolts 50 (sleeve 20) and 51 (sleeve 21) which are removably engaged by wing nuts 52 and 53. The details of this connection are seen on sleeves 20 and 21 in FIGS. 1, 3, 5 and 7–9, inclusive. The mechanism of operation of the arm rest upon loosening of the wing nuts 52 and 53 on bolts 50 and 51 which pass through the flattened portions of the lengths of sleeves 20 and 21 will be later described, with respect to the pivotable elevation of the head end of the frame and the engagement of the portions of the arm rest with parts of the frame.

A first pair of bearing collars 54 and 55 are fixed by suitable conventional means to each underside of tops 40 and 41 of the A-frames. A first cylindrical shaft is rigidly received and fixed in said bearing collars, the shaft numbered 56. A pair of second bearing collars (FIG. 7) 57 and 58 are each fixed to one underside of the elongate sleeve members 20 and 21, respectively, intermediate the ends thereof and past the pivotal connection of the sleeves for the chair back construction toward the foot end. The latter bearing collars 57 and 58 pivotally engage the first cylindrical shaft 56 inboard of the first bearing collars 54 and 55. Thus it can be seen that the normally horizontal frame may pivot on shaft 56 with respect to the A-frame base support members. This capacity of the horizontal frame to pivot with respect to the base is controlled and effected in a manner to be described in detail.

Figure 11:
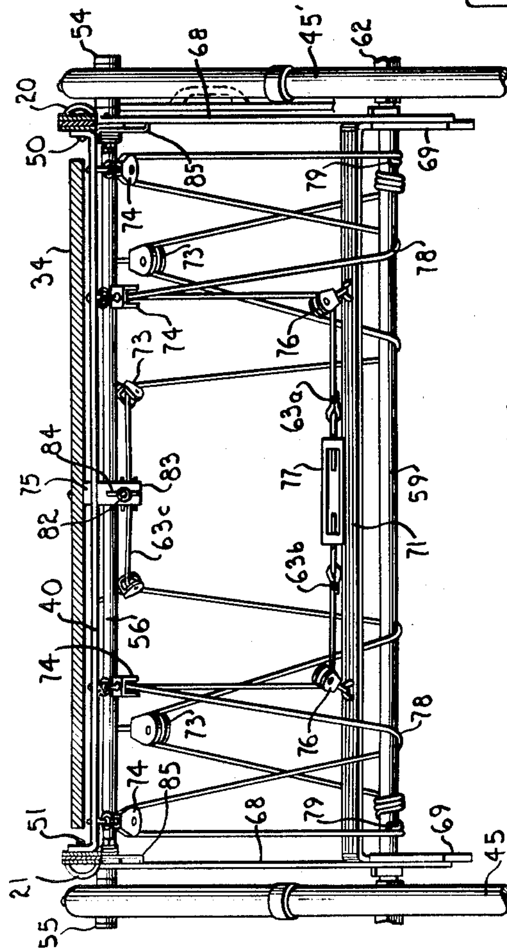
FIG. 11 is a view taken along the line 11—11 of FIG. 1 in the direction of the arrows.

A second cylindrical shaft 59 is rotatably received through openings in plates 48 through suitable bearing members 62 fixed thereto (FIGS. 7, 11 and 12), there being fixed to the outer ends of shaft 59 (outboard of plates 48) two wheels 60 and 61. Rotation of shaft 59 is effected by rotation of wheel 60 and 61.

Elongate resilient cable means 63, in a manner to be described, couples the transverse beam members 39 and 40 and the second cylindrical shaft 59 in such fashion that rotation of shaft 59 in one direction (wheel 61 clockwise in FIG. 1) will angle the body receiving frame from the horizontal with the head end downward and the foot end upwards. Rotation of second cylindrical shaft 59 in the other direction (wheel 61 counterclockwise in FIG. 1) will return the body receiving frame from the said downwardly angled head position towards and to the horizontal position of the frame. The cable means 63 is also coupled to a locking device for securing the horizontal and extreme inclined positions of the body receiving frame. Such will first be described, and thereafter the cable connecting and tensioning means and operation thereof. With respect to these details, reference is made particularly to FIGS. 7–9, inclusive and 11 and 12. Means 63 may be a cable of metal or plastic, but preferably is a rope of conventional and more resilient material than wire.

Figure 12:
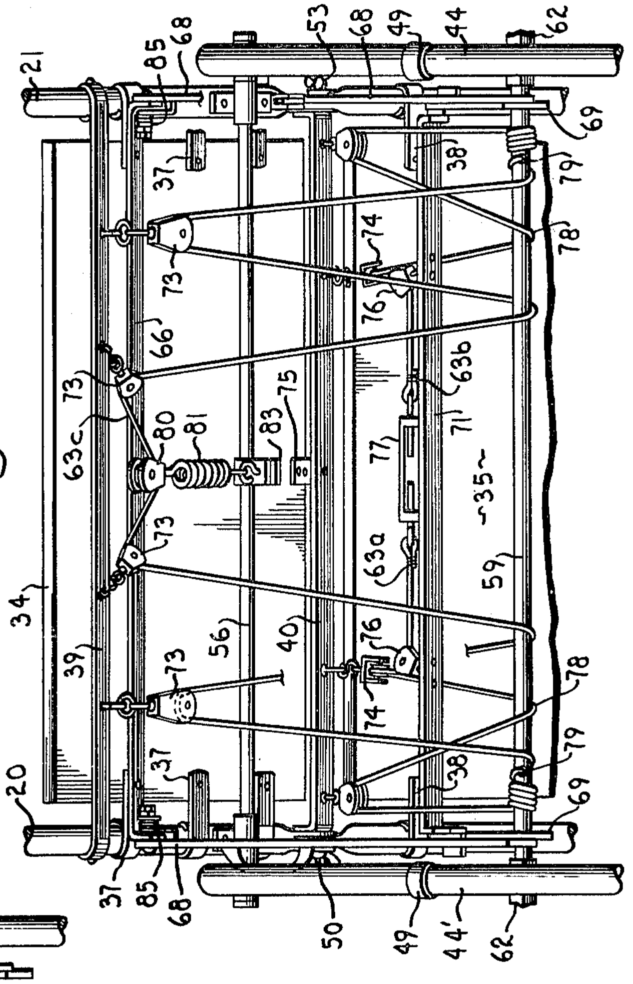
FIG. 12 is a view taken along the line 12—12 of FIG. 2 in the direction of the arrows.

The locking device for securing the horizontal and inclined positions of the body receiving frame involves a pair of arms 68, one secured to each downwardly extending end 65 of a strap 66 which is connected by collars 67 to sleeves 20 and 21 next to but toward the head end of the frame from transverse member 39. While these arms are paired and at each side of the horizontal frame, only one of them will be described in detail (that seen in FIGS. 8 and 9), all parts of both arms being numbered the same. Strap 66 underlies and is connected to two of the straps 37 supporting plate 34 adjacent its ends (FIG. 12).

Each arm 68 has an upper and a lower end, the upper end being pivotally connected as at **68*a* to flange or member 65. That is, one of said arms is pivotally mounted from its upper end on the underside of each elongate sleeve 20 and 21 intermediate the ends thereof and offset toward the foot end of the frame from the first cylindrical shaft 56. A cage frame 69 is fixed to the lower end of each said arm 68 and has a closed trackway 70 therein of substantial numeral 7 configuration opening toward the head end of the frame. The second cylindrical shaft 59 extends through the cage frames 69 on arm 68 within the trackways 70. A transverse connecting beam 71 joins to the two arms 68 and extends therebetween, spacing them apart, whereby the two arms 68 and transverse connecting beam member 71 make up a U-frame pivotally suspended beneath the body receiving frame and coupled to the second cylindrical shaft by the cage frames and trackways 70** therewithin.

Turning now to the cable drive of the subject device in question, a plurality of pulleys 73 are provided connected to transverse member 39 by suitable hooks. A second plurality of pulleys 74 are likewise provided connected by suitable hooks or means to transverse member 40. Transverse member 40, incidentally, has center strap 75 connected centrally thereof and also to plate or member 34 for rigidity. Likewise member 39 may be connected centrally to board or member 34 for rigidity. A pair of pulleys 76 are mounted on transverse beam member 71 which interconnects and spaces apart the arms 68 of the locking device previously described.

Between pulleys 76 there is provided a conventional double ended turnbuckle 77 to which the free ends of the single cable member 63 are connected at **63*a* and 63*b*. The hook members by which the sets of pulleys 73, 74 and 76 are connected to beam members 39, 40 and 71 are numbered 73*a*, 74*a* and 76*a*, respectively. As may be seen particularly in FIGS. 7, 11 and 12, the cable 63, from the free end connection 63*a* and 63*b* thereof to turnbuckle 77, passes outwardly through pulleys 76, thence through the inboard pulleys 74 on beam 40 and thereafter loops around the rotatable shaft 59. This first loop is designated, at its contact with shaft 59, 78. Thereafter, cable 63 passes to the outboard set of pulleys 74 and from there back to and wrapping around rotatable shaft 59. A pair of openings or holes 79 are provided through shaft 59 adjacent to, but short of, plates 48, through which passes cable 63. After this passage through shaft 59, the cable or rope 63 is several times wrapped around shaft 59 and thence passes toward the foot end of the device (to the left in FIG. 7) to engage the outboard pulleys 73 of the set of pulleys on beam 39. After this engagement, cable or rope 63 passes back to, over and around shaft 59 and thence to the inboard pair of pulleys 73 on beam or member 39. It is the center length of the cable or rope 63 as at 63*c* which passes over a final pulley 80 which is connected to a cable tightening or tensioning spring 81. Spring 81 is connected at its other end to the loop 82*a* of an elongate bolt 82 which is received through clip 83 on nonrotating shaft 56. Wing nut 84 on the elongate bolt 82** gives further tightening adjustment availability.

Thus it is seen that cable or rope tightening means are provided at the free ends of the cable **63*a* and 63*b* with turnbuckle 77 and, additionally, the tightening means comprising bolt 82 at the middle portion 63 of the cable also has tensioning spring 81 associated therewith. As noted, the cable or rope 63 connects at its free ends onto beam 71 which is connected to arms 68 having cages 69 with slots 70 therein. By virtue of the sets of pulleys 74 on beam 40 and 73 on beam 39, the cable is connected with the frame on each side of the pivotal connection of the bearings 57 and 58 on rigid shaft 56**.

Figure 8:
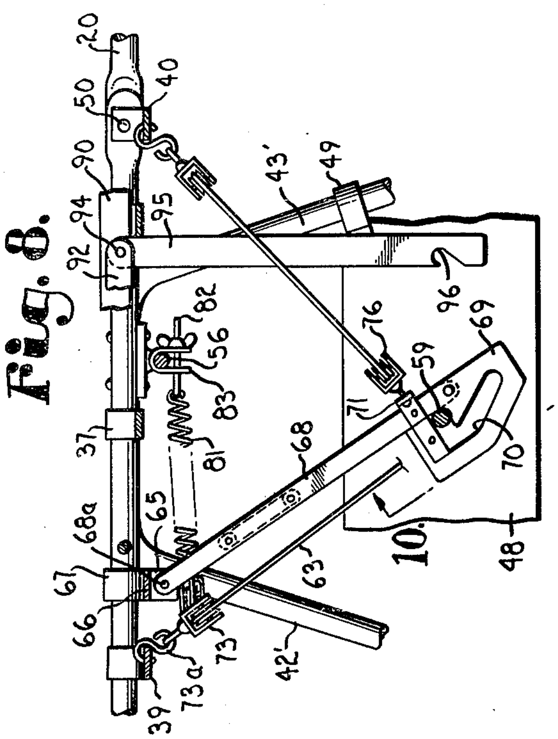
FIG. 8 is a fragmentary, side elevation of the upper portion of the angling and return mechanism of FIG. 7, with the device in level position and locked therein.

The operation of the cable drive system and of the locking mechanism may now be described. This action starts from the position of FIG. 8 with shaft 59 in the upper and end portion of slot 70. The cable is taut and, since a weight placed either side of shaft 59 on the horizontal frame plates 33, 34 or 5 will merely either jam the top of cage 69 down on shaft 59 (weight at foot) or the bottom of the slot portion in which shaft 59 is seen in FIG. 8 up against shaft 59 (head end weight), the frame is locked in horizontal position. At this point, the operator, who is presumably lying in the frame with his feet hooked in the member 22 as previously described and his head at the other end of the frame, rotates wheel 61 clockwise in the view of FIG. 1. This rotates shaft 59 clockwise in the views of FIGS. 8 and 9 and, because of the cable engagement with holes 79 in shaft 59, as well as the wraps of cable therearound, pulls the cable to shorten it on the right hand side of the view of FIG. 7. This action rotates the body receiving frame from horizontal (FIG. 8) clockwise around shaft 56 toward the cable shortest position at the head end of the frame seen in FIG. 11 and, at the same time, to the cable lengthened position on the foot end of the frame to the foot up, head down angled position seen in FIG. 12.

Figure 9:
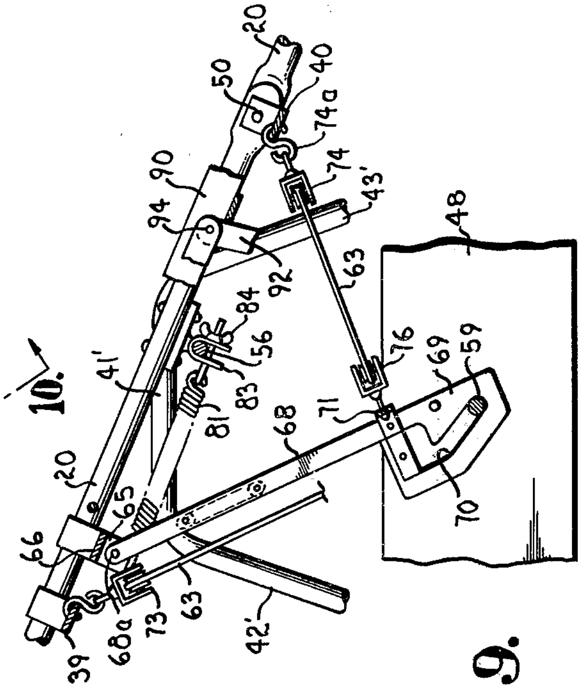
FIG. 9 is a view like that of FIG. 8, except with the device angled to the extreme position of FIG. 2.
Figure 7:
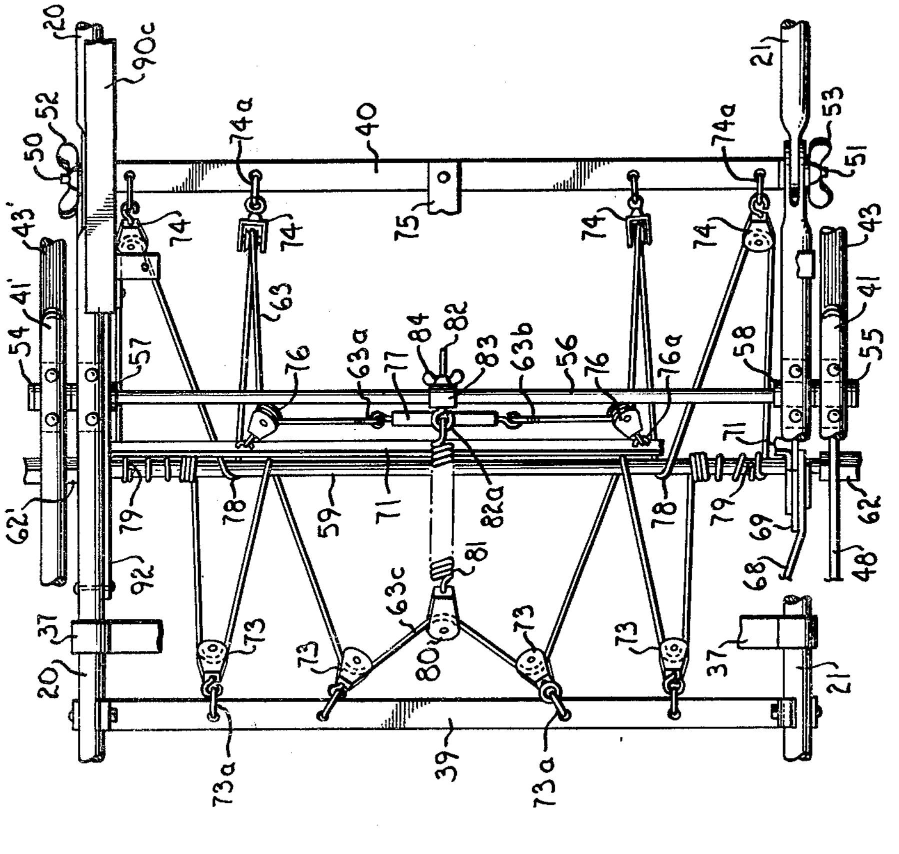
FIG. 7 is a plan view, from above, of the center of the device, showing the elements of the angling and return system (that is, a plan view of the center portion of FIG. 4, with the center upper panel removed from the frame, and looking downwardly in the view).

What happens is that, as the cable shortens on the right side of FIGS. 7–9, inclusive, arms 68 are pivoted in a counterclockwise direction in the views of FIGS. 8 and 9, thus pulling cage 69 free of shaft 59 which then moves down slot 70 into the end position seen in FIG. 9. At the latter point, the normally horizontal frame is in the head down position of FIG. 2 with cross member 28*c* abutting the level floor or base. As mentioned, shaft 59 is translated from a first locking position as seen in FIG. 8 to a second locking position as seen in FIG. 9. The cable tensioning spring 81 is under considerable tension and expansion in the horizontal position of the frame as may be seen in FIG. 8 and under relaxation in the position of FIG. 9.

The cable in the left hand portions of the views of FIGS. 7–9, inclusive (to the left of shaft 59) is under considerable tension when the frame is in horizontal position. Such lessens as the head end of the frame is pulled downwardly. The arms 68 are spring loaded (as at 85) with respect to sleeves 20 and 21 tending to move them at all times in a clockwise direction around their pivot mounting 68*a* (in the views of FIGS. 8 and 9). As the clockwise rotation of the wheel 61 begins and continues, there is a cable tightening on the right hand side of the cable system in FIGS. 7–9, inclusive to pull up beam 71 and pull down the frame end by exerting force on beam 40 from shaft 59. When the device is in the inclined position of FIGS. 2, 9, 11 and 12, the shortened cable on the head end (right hand sides of FIGS. 7–9, inclusive) is pulling from turnbuckle 77 through pulleys 76, into the first inboard set of pulleys 74 against shaft 59 at 78 and into the pulleys 74 outboard on member 40, thence to the wraparound of shaft 59 and openings 79 therethrough. This is the force system which maintains the frame inclined in the position of FIGS. 2, 9, 11 and 12 with shaft 59 locked in the bottom of slot 70 as seen in FIG. 9.

With the arms 68 pivoted counterclockwise in the views of FIGS. 8 and 9 by the cable tightening on the right hand side of shaft 59 (and shaft 56), once shaft 59 hits the opposite end of the top portion of slot 70 from that seen in FIG. 8, the rising left hand side of the frame pulls arm 68 and cage 69 upwards so shaft moves down in slot 70 to the FIG. 9 position.

Turning shaft 61 counterclockwise in the views of FIGS. 1 and 2 reverses this action with the cable in the left hand side of FIGS. 7–9, inclusive pulling from the wrap around shaft 59 following openings 79 through pulleys 73 on beam 39, thus pulling the frame back to the horizontal position. As shaft 59 rises up slot 70 and ultimately to the position seen in FIG. 8, further rotation of the wheel 61, counterclockwise in the view of FIG. 1, pulls on the chain tightening or tensioning spring 81, extending it. Thus, rotation of the wheels in one direction tightens the cable on one side of shaft 59, pulling on the connection elements on that side and tilting the frame in one direction or the other. Rotation of the wheels in the other direction tightens the cable on the other side of shaft 59, reversing the action. By the provision of the lever arms 68, cages 69 and slots 70, definite action limits and locks are provided at each end of the cycle.

Turning back to the chair back of FIGS. 3 and 5, as previously mentioned, the elongate side sleeves or members 20 and 21 are hinged around bolts or pins 50 and 51 between the first cylindrical shaft 56 and the head end of the frame, whereby the head end of the frame may be pivoted upwardly to substantial right angles with the center and foot end of the frame, thereby to form a chair configuration. An arm rest configuration is provided on each side of the body receiving frame. The parts of both arm rests will be numbered the same in the views.

Each rest includes a first piece or member 90 (FIG. 5) pivotally mounted on one end 90*a* by pin 91 to the elongate side member or sleeve 20 or 21 past the hinge at pins 50 and 51 towards the head end of the frame. A second piece or member 92 is pivotally mounted at one end 92*a* to the elongate side members 20 or 21 past the hinges at 50 or 51 by pin 93. The two pieces 90 and 92 are pivotally joined by pin 94 at their free ends 92*b* and 90*b*. Member 90 has flange 90*c* adapted to overlie the sleeves 20 and 21 when the frame is fully extended and receives the forearms of the user of the device when the arm rest is erected and in use.

Third arms or pieces 95 are pivotally mounted on pins 94 at one end thereof and have slots 96 formed in the opposite end sides thereof so that they may be employed to engage shaft 56. The latter lock plus the friction binding means (wing nuts) on pins 50 and 51 stabilize the head end of the frame in raised position and arm rest in the erect position of FIGS. 3 and 5.

By releasing or loosening the wing nuts 52 and 53 and moving the head end of the frame counterclockwise in FIGS. 3 and 5, the members 95 may be disengaged from shaft 56 so that the head end of the frame may be put into the horizontal position as seen in FIGS. 1, 2 and 4.

When the device is in the horizontal position of FIGS. 1, 2 and 8, the springs 85 loading of arms 68 (which tend to move the arms 68 in a clockwise direction around pivot 68*a*) will maintain the device in locked position as in FIG. 8 even if the cable or rope is severed.

The typical maximum angle of recline (from the horizontal) useable is 25 to 33 degrees.

USE OF THE DEVICE (1) For proper use of the device by an individual, the body-receiving frame must be in a horizontal position. To obtain this position, the tilt wheels are turned (the operator pushes forwardly from the top of the wheels) as far as they will go so that the frame horizontal lock is actuated. The cushioned upright end is the forward or foot end.

(2) The individual or operator sits in the center of the frame, on the center section thereof, with his feet dropped to the floor, over the wheel, on either side of the device. The operator, by instructions supplied with the subject device, is never to sit on either end of the frame, only at the center thereof.

(3) The operator swings his feet up and onto the forward or foot end of the frame, still in the sitting position.

(4) The operator inserts his feet between the upper and lower, cushioned, cross-members on the foot end of the frame, making sure his heels are hooked behind the lower cross tube and the toes are inserted behind the upper, curved tube. The operator preferably spreads his feet as far apart as possible until his toes are under the rounded part of the upper cross tube.

[The position of the paired cross tubes at the foot end of the body-receiving frame is previously adjusted to the proper leg length.]

(5) With his hands, the operator pushes the lower part of his body backwards, toward the head end of the bed, as far as possible on the frame, in order to tighten the toe and heel positions. The operator then lies back, outstretched, on the frame.

(6) The operator then begins tilting the frame downwardly at the head end and upwardly at the foot end by, preferably, alternating one hand and then the other, pulling the tops of the wheels backwards or toward the head end of the frame.

[The operator may stop at any incline angle desired. The tilt will hold at any angle reached. Alternatively, the operator may continue the wheel action until the downwardly inclined cross tube of the head end touches the floor. Resistance to the wheel pull tells the operator when the head is lowered to maximum angle. The operator should not continue the wheel pull after this resistance is felt.]

(7) The operator stays on the frame in the tilted position, relaxing and resting, but preferably not longer than 15 minutes for the first few trials. The operator should keep his hands on his stomach or on the top of the wheels when in full tilt position. The operator should not put his hands under the frame.

(8) If, while in the full tilt position, the operator's heels should disengage from the lower cross tube and the operator's body slide downwardly, the operator should not try to elevate the frame to the horizontal position. If the body balance on the bed is impaired, the frame (and the body thereon) cannot readily be elevated to the horizontal position. The remedy is to push the body backwards and downwardly off the bed toward the head onto the floor. The operator should then get up and start over again. This action will not happen, however, if a firm heel lock is made, with the feet to the side of the frame, before the tilting is started. The operator should never disengage his heels while in a tilted position.

(9) In order to return to a horizontal position, the operator pushes the tops of the wheels forwardly (toward the foot end of the frame), alternating one hand then the other. The operator pushes the wheels forwardly as far as possible to engage the horizontal lock, but stops when the wheel push resistance is felt.

(10) Thereafter, the operator disengages his heels and lies in the horizontal position on the frame a minute or two, relaxing. Then, with each hand extended, the operator holds the underside of the frame and, with pressure on his elbows, raises his body to a sitting position. The operator then swings his legs around, off the bed, and places his feet on the floor. At this point, the operator may get off the frame.

It is well for the operator to test the tilting action of the frame and its return before getting on it and using it each time. Specifically, the operator should move the frame to full tilt and return it to the horizontal position, in order to see that it is in perfect working order and that no cord is severed or any part of the drive mechanism inoperative.

From the foregoing, it will be seen that this invention is one well adapted to attain all of the ends and objects hereinabove set forth together with other advantages which are obvious and which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

I claim:

1. A therapy device comprising, in combination:

a pair of parallel oriented A-frame members adapted to rest on a floor or ground surface with the lower ends of the legs of the A, a pair of first bearing collars, one fixed to each underside of the tops of the A-frames, a first cylindrical shaft rigidly received in said first bearing collars, an elongate, rectangular, body-receiving frame having elongate side members and transverse end members, the said body-receiving frame configured at the ends thereof so as to provide a downwardly angled head end and an upwardly angled foot end, a pair of second bearing collars, one fixed to each underside of the elongate side members of the body-receiving frame intermediate the length thereof pivotally engaging the first cylindrical shaft inboard of the first bearing collars, two opposed, substantially parallel plate members, one carried between each pair of A-frame legs and fixed thereto, a second cylindrical shaft rotatably received between said two plate members and extending therethrough, a turning wheel removably fixed to each end of said second shaft outside of the said plate members, a pair of transverse beam members, each extending between and fixed to the said members of the body-receiving frame intermediate the ends thereof, one on each side of said first and second cylindrical shafts, elongate, resilient cable means coupling the said latter transverse beam members and the second cylindrical shaft, whereby rotation of the latter in one direction angles the body-receiving frame from the horizontal with the head end downward and foot end upwards and rotation of the second cylindrical shaft in the other direction returns the body-receiving frame towards the horizontal position thereof, the downwardly angled head end of the body-receiving frame and the upwardly angled foot end of same each having a transverse beam member extending between and connecting the elongate side members at the ends of the straight portions thereof and immediately before the upwardly and downwardly angled head end and foot end, respectively, and body carrying, transverse support members provided communicating between and carried by the elongate side members along the lengths thereof between said cushioned transverse beams adjacent the ends of said body-receiving frame.

2. A device as in claim 1 wherein the upwardly angled foot end of the frame is longitudinally adjustable with respect to the elongate side members of the frame in order to allow for different leg lengths of users of the device.

3. A device as in claim 1 wherein the transverse beam members adjacent the head and foot ends of the frame and the upwardly angled foot end of the body-receiving frame are cushioned along the lengths thereof.

4. A device as in claim 1 wherein the body carrying transverse support members comprise three rigid plates, one said plate overlying the said two cylindrical shafts substantially at the center of said frame, the other two plates positioned between the center plate and the head and foot transverse beam members and means coupling each of said plates to said elongate side members in removable fashion.

5. A device as in claim 1 including a locking device for securing the horizontal and inclined extreme positions of the body-receiving frame comprising:

a pair of arms, each said arm having a lower and an upper end, one said arm pivotably mounted from its upper end on the underside of each said elongate side member intermediate the ends thereof and off-set towards the foot end of the frame from the first cylindrical shaft, a cage frame on each lower end of the arm having a closed trackway therein of substantial numeral 7 configuration opening towards the head end of the frame, the second cylindrical shaft extending through said cage frames within said trackways, a transverse connecting beam joining the two arms adjacent the cage frames thereon and spacing them apart, whereby the arms and transverse connecting beam make up a U-frame pivotably suspended beneath the body-receiving frame and coupled to the second cylindrical shaft by said cage frames, and the free ends of the cable member engaged with said transverse connecting beam, whereby the second cylindrical shaft is drawn into the upper leg of the 7 configuration trackways in the cage beams for locking purposes when the body-receiving frame is substantially horizontal and into the lower leg of the 7 configuration trackways in the cage beams for locking purposes when the body-receiving frame is inclined head downward and foot upward.

6. A device as in claim 5 including cable tightening means associated with the free ends of the cable.

7. A device as in claim 5 including cable tensioning means cooperating between the first cylindrical shaft and the cable.

8. A device as in claim 1 wherein the elongate side members of the body-receiving frame are hinged between the first cylindrical shaft and the head end of the frame, whereby the head end of the frame may be pivoted upwardly to substantial right angles with the center and foot end of the frame, thereby to form a chair configuration, an arm rest on each side of the body-receiving frame, each rest comprising a first piece pivotably mounted on one end thereof to the elongate side member past the hinge to the head of the frame, a second piece pivotably mounted to the elongate side member past the hinge to the foot of the frame, the two pieces pivotably joined at their free ends, and means for removably locking the frame in the chair configuration comprising third pieces each pivotably connected at one end to the end connections of one set of the first and second pieces and having the other ends thereof arcuately relieved to overlie and engage the first cylindrical shaft, and friction binding means at the side member hinges.

* * * * *